US006458804B1

(12) United States Patent
Cutler et al.

(10) Patent No.: US 6,458,804 B1
(45) Date of Patent: Oct. 1, 2002

(54) METHODS FOR THE TREATMENT OF CENTRAL NERVOUS SYSTEM DISORDERS IN CERTAIN PATIENT GROUPS

(75) Inventors: Neal R. Cutler, Los Angeles; John Sramek, Irvine, both of CA (US)

(73) Assignee: R.T. Alamo Venturesi, LLC, Beverly Hills, CA (US)

( * ) Notice: Subject to any disclaimer, the term of this patent is extended or adjusted under 35 U.S.C. 154(b) by 0 days.

(21) Appl. No.: 09/772,321

(22) Filed: Jan. 26, 2001

(51) Int. Cl.$^7$ .............................................. A61K 31/47
(52) U.S. Cl. ...................................................... 514/312
(58) Field of Search ........................................ 514/312

(56) References Cited

U.S. PATENT DOCUMENTS

| | | | |
|---|---|---|---|
| 4,277,479 A | 7/1981 | Nishi et al. ................. | 424/258 |
| 4,302,460 A | 11/1981 | Davies et al. ............... | 424/258 |
| 4,522,884 A | 6/1985 | Brody ........................ | 428/400 |
| 4,552,891 A | 11/1985 | Ho et al. .................... | 514/443 |
| 4,623,650 A | 11/1986 | Gilligan et al. ............. | 514/312 |
| 4,710,506 A | 12/1987 | Davies et al. ............... | 514/301 |
| 4,772,614 A | 10/1988 | Davies et al. ............... | 514/312 |
| 4,855,291 A | 8/1989 | Davies ....................... | 514/312 |
| 4,877,793 A | 10/1989 | Davies ....................... | 514/301 |
| 4,997,840 A | 3/1991 | Davies et al. ............... | 514/312 |
| 5,011,931 A | 4/1991 | MacLean et al. ........... | 546/155 |
| 5,079,264 A | 1/1992 | MacLean et al. ........... | 514/629 |
| 5,393,773 A | 2/1995 | Craig et al. ................. | 514/415 |
| 5,554,639 A | 10/1996 | Craig et al. ................. | 514/415 |
| 5,627,191 A | 6/1997 | Birch et al. ................. | 514/303 |
| 5,670,539 A | 9/1997 | Richardson et al. ........ | 514/561 |
| 5,868,473 A | 11/1997 | Cosford et al. ............. | 514/357 |
| 5,731,314 A | 3/1998 | Bencherif et al. .......... | 514/256 |
| 5,767,116 A | 6/1998 | Kerrigan et al. ............ | 514/212 |
| 5,801,161 A | 10/1998 | Merkus ........................ | 514/52 |
| 5,864,037 A | 1/1999 | Chasin et al. ............... | 544/118 |
| 5,869,479 A | 2/1999 | Kreutner et al. ............ | 514/212 |

FOREIGN PATENT DOCUMENTS

WO     WO 94/02144     3/1994

OTHER PUBLICATIONS

MEDLINE No. 99005735, Torigoe et al, No To Shinkei, Brain and Nerve, Sep. 1998, 50 (9) 829–39, abstract.*
BIOSIS 1993:98778, Ikezono et al, Arzneimittl–Forschung, 1992, 42(10), 1200–1211, abstract.*
McMurry, *Organic Chemistry, 2nd Ed.*, Brooks/Cole Publishing, Belmont, CA (1988), pp. 1044–1045 and 1076.
Kelso et al., "Actions of the Novel Vasodilator, Flosequinan, in Isolated Ventricular Cardiomyocytes," *J. Cardiovasc. Pharmacol.* 25:376–386 (1995).
Perreault et al., "Differential inotropic effects of flosequinan in ventricular muscle from noemal ferrets versus patients with end–stage heart failure," *Br. J. Pharmacol.* 106:511–516 (1992).
Jones et al., "Effect of flosequinan on ischaemia–induced arrhythmias and on ventricular cyclic nucleotide content in the anaestetized rat," *Br. J. Pharmacol.* 108:1111–1116 (1993).
Gristwood et al., "Studies on the cardiac actions of flosequinan *in vitro*," *Br. J. Pharmacol.* 105:985–991 (1992).
Frodsham et al., "Effect of flosequinan upon isoenzymes of phosphodiesterase from guinea–pig cardiac and vascular smooth muscle," *Eur. J. Pharmacol.* 211:383–391 (1992).
Dawson et al., "Cilostazol Has Beneficial Effects in Treatment of Intermittent Claudication," *Circulation* 98:678–686 (1998).
Elam et al., "Effect of the Novel Antiplatelet Agent Cilostazol on Plasma Lipoproreins in Patients with Intermittent Claudication," *Arterioscler Thromb. Vasc. Biol.* 18:1942–1947 (1998).
Drug Evaluation Monographs, vol. 99, Micromedex Inc. (1999).
Nishi et al., "Studies on 2–Oxoquinoline Derivatives as Blood Platelet Aggregation Inhibitors. II. 6–[3–(1–Cyclohexyl–5–tetrazolyl)propoxy]–1,2–dihydro–2–oxoquinoline and Related Compounds," *Chem. Pharm. Bull.* 31:1151–1157 (1983).
Shimizu, T. et al., "Physico–chemical Properties and Stability of Cilostazol," *Arzneim.–Forsch.* 35:1117–1208 (1985).
Suri et al., "Pharmacolinetics of Multiple–Dose Oral Cilostazol in Middle–Age and Elderly Men and Women," *J. Clin. Pharmacol.* 38:144–150 (1998).
Niki and Mori, "Phase I Study od Cilostazol," *Arzneim.–Forsch* 35:1173–1185 (1985).
Watkins, CC et al. "Insulin restores neuronal nitric oxide synthase expression and function that is lost in diabetic gastropathy" *J Clin Invest* 106:373–384 (2000).
Moreira et al., "Side–effect profile of sildenafil citrate (Viagra) in clinical practice," *Urology*, 56(3):474–76 (2000).
Morita et al., "Synthesis and Absolute Configuration of the Enantiomers of 7–Fluoro–1–methyl–3(methylsulfiny)–4(1H)–quinolonone (Flosequinan)." *Chem. Pharm. Bull.* 42(10):2157–2160 (1994).
Robertson M., "Tourette Syndrome, associated conditions and the complexities of treatment," *Brain* 123:425, 427 (2000).
Juncos, J. and Delong, M., "Parkinson's disease and basal ganglia movement disorders", in *Scientific American Medicine*, Rubinstien and Federman eds., Ch. 11, pp. XV–1 to XV–19 (1997).

* cited by examiner

Primary Examiner—Rebecca Cook
(74) Attorney, Agent, or Firm—Medlen & Carroll, LLP

(57) ABSTRACT

Methods and compositions for treating specific patient groups for Central Nervous System disorders, including but not limited to Tourette Syndrome, are provided. The methods of the present invention comprise the utilization of pharmaceutical compositions comprising quinolinones (and derivatives thereof) in patients with symptoms of a Central Nervous System Disorder who are otherwise free of cardiac disease and/or who have not been given organic nitrates.

19 Claims, 2 Drawing Sheets

METHODS FOR THE TREATMENT OF CENTRAL NERVOUS SYSTEM DISORDERS IN CERTAIN PATIENT GROUPS

FIELD OF THE INVENTION

The present invention relates to methods and compositions for the treatment of Central Nervous System (CNS) disorders, including but not limited to Tourette Syndrome, in adults and children. The methods of the present invention comprise the utilization of pharmaceutical compositions to patients who are free of symptoms of cardiac disease and who have not been treated with drugs which cause hypotensive effects, such as nitrites and nitrates.

BACKGROUND

Tourette Syndrome (TS) is an autosomal dominant neuropsychiatric disorder affecting up to one person in 2,500 and is characterized by a range of neurological and behavioral symptoms. Such symptoms include: (A) the presence of both motor and vocal tics at some time during the illness, although not necessarily concurrently; (B) the occurrence of quasi-daily tics throughout a period of time exceeding one year; (C) variance in the clinical phenomenology of the tics; and (D) marked distress or significant impairment in social, occupational, or other important areas of functioning. Patients with TS also often suffer from co-morbid disorders such as Obsessive-Compulsive Disorder (OCD), Attention-Deficit Hyperactivity Disorder (ADHD), anxiety disorders, mood disorders, and panic disorders.

Tics experienced by a sufferer of TS can be transient or acute, and simple or complex. Motor tics generally include eye blinking, nose twitching, grimacing, muscle tensing, hopping, touching objects or others, and rapid jerking of any part of the body. Vocal or phonic tics typically include coughing, spitting, grunting, barking, hissing, sucking sounds, gurgling, screeching, whistling, palilalia, echolalia, and coprolalia.

The etiology and pathophysiology of TS are currently unknown. However, pharmacological and metabolic evidence suggests the involvement of several neurochemical systems, such as the dopaminergic, noradrenergic, GABAergic, and serotonergic mechanisms for example, and implicates neurotransmission dysfunction with the disorder.

Historically, attempts at treating TS by psychotherapeutic and behavior modification approaches were not encouraging in terms of dramatic, lasting improvement. Thus, the pursuit of behavioral strategies for decreasing the occurrence of tics has diminished. Current treatment of TS includes the administration of medications which are prescribed for neurotransmitter disorders. For example, neuroleptic drugs (i.e. those which reduce the amount of dopamine in the CNS) such as haloperidol, pimozide, fluphenazine, and chloropromazine have been administered to TS patients with success, but with side effects such as tardive dyskinesia, akinesia, increased appetite and weight gain, amenorrhea, Q and T wave changes, hypotension, and impotence. Other drugs such as clonidine (an antihypertensive), clonazepam (an anticonvulsant), and various antidepressants have been used to treat TS symptoms, but also induce side effects in the patient such as, for example, impotence.

Moreover, compounds that modulate activity of various receptors have been suggested as treatment due to a decreased number of receptors in the brains of patients suffering CNS disorders. (Cosford et al., U.S. Pat. No. 5,868,473 and Kerrigan et al., U.S. Pat. No. 5,767,116). Additionally, nicotine pharmacology has been suggested in suppressing TS. (Bencherif et al., U.S. Pat. No. 5,731,314). It has also been suggested that TS is caused by the supply of tryptophan to the brain, and TS symptoms have been treated by regulating the supply of tryptophan to the brain. (Richardson et al., U.S. Pat. No. 5,670,539).

Stimulants such as methylphenidate, dextroamphetamine, and pemoline may be prescribed for hyperactivity and ADHD, but often lead to an increase in the tics in TS. Antidepressants such as fluoxetine and clomiprimine are often prescribed to treat OCD symptoms. However, such antidepressants may also induce side effects such as muscle weakness, seizures, constipation, and impotence.

Although other pharmacological methods of treatment of TS are available, such methods have not proven to be highly satisfactory and can be accompanied by severe side-effects. What is needed is an improved method for the treatment of CNS disorders, including but not limited to Tourette Syndrome, without the induction of side effects in the patient such as, for example, impotence.

SUMMARY OF THE INVENTION

The present invention relates to methods and compositions for the treatment of Tourette Syndrome and other central nervous system disorders in adults and children. The methods of the present invention comprise the utilization of pharmaceutical compositions to patients who have symptoms of TS, but who are otherwise free of symptoms of cardiac disease and who have not been treated with drugs which cause hypotensive effects, such as nitrites and nitrates. The compositions comprise quinolinones, including derivatives and purified enantiomers thereof. Quinolinones are also known as quinolones and oxo-quinolines.

It is not intended that the present invention be limited by the nature of the derivative. In one embodiment, the quinolinones derivative is cilostazol (6-[4-(1-cyclohexyl-1-H-tetrazol-5-yl)butoxyl]-3,4-dihydro-2(1H)-quinolinone; 6-[4-(1-cyclohexyl-1H-tetrazol-5-yl)butoxy]-3,4-dihydrocarbostyril; 6-[4-(1-cyclohexyl-5-tetrazoyl)butoxy]-1,2,3,4-tetrahydro-2-oxoquinoline).

In yet other embodiments, metabolites of cilostazol are contemplated for use in the methods of the presently claimed invention. Metabolites of cilostazol include, but are not limited to monohydroxycilostazol, monohydroxydehydrocilostazol, 3,4-dihydro-6-hydroxy-2 (1H)-quinolinone, their conjugates and dehydrocilostazol.

In one embodiment, the present invention contemplates halogenated quinolinones (e.g., fluoroquinolinone). In a preferred embodiment, the quinolinone is a thioquinolinone or a sulphinyl or suphonyl derivatives thereof. In one embodiment, the halogenated quinolinone is flosequinan (7-fluoro-1-methyl-3-methylsulphinyl-4-quinolone). In a preferred embodiment, an enantiomer of flosequinan is used.

In one embodiment, the present invention contemplates a method, comprising: a) providing: i) an adult or child with symptoms of a Central Nervous System (CNS) disorder, and ii) flosequinan; and b) administering said flosequinan to said adult or child. It is not intended that the present invention be limited to symptoms of Tourette Syndrome (TS). A variety of such symptoms are contemplated, including but not limited to, motor and vocal tics. In one embodiment, the present invention contemplates administering said flosequinan to said adult or child under conditions such that frequency and/or severity of tics of said adult or child is diminished.

In another embodiment, the method comprises providing: i) an adult or child with Tourette Syndrome, and ii) flosequinan; and introducing said flosequinan to adult or child (e.g. such that the symptoms of Tourette Syndrome of said adult or child are reduced).

In another embodiment, the present invention contemplates a method, comprising: a) providing: i) a male or female with symptoms of Tourette Syndrome, and ii) a composition comprising a quinolinone selected from the group consisting of a racemic mixture of flosequinan and an enantiomer of flosequinan; and b) administering said composition to said male or female (e.g. such that said symptoms are reduced). A variety of such symptoms are contemplated, including but not limited to, motor and vocal tics. In one embodiment, the present invention contemplates administering said composition to said adult or child under conditions such that frequency and/or severity of tics of said adult or child is diminished.

In a preferred embodiment, the male or female is an adult human and the oral dosage of flosequinan is in a single dose per day of up to approximately two hundred milligrams, and more preferably, between approximately ten to approximately seventy-five milligrams. In another preferred embodiment, flosequinan is administered in a single oral dose per day of between approximately one hundred and ten and approximately two hundred milligrams. In another preferred embodiment, the male or female is an adult human and the oral dosage of flosequinan is in three daily doses, before meals, each dose of up to approximately two hundred milligrams, and more preferably, between approximately ten to approximately seventy-five milligrams. In another preferred embodiment, flosequinan is administered in three oral doses per day, before meals, of between approximately one hundred and ten and approximately two hundred milligrams. In other embodiments said flosequinan is introduced cutaneously, by standard injection (e.g intravenously or intramuscularly), or intranasally.

In one embodiment, the method comprises a) providing: i) a subject (whether adult or child) suffering from symptoms of a CNS disorder who is free from cardiac disease; and ii) flosequinan; and b) introducing said flosequinan to said subject (e.g. such that said symptoms are reduced). A variety of such symptoms are contemplated, including but not limited to, motor and vocal tics. In one embodiment, the present invention contemplates administering said composition to said adult or child under conditions such that frequency and/or severity of tics of said adult or child is diminished. In another embodiment, said subject suffering from symptoms of a CNS disorder is not free from cardiac disease.

In another embodiment, the method comprises a) providing: i) a subject (whether adult or child) suffering from symptoms of a CNS disorder who is not being treated (and/or has not been treated in the past) with a drug that causes hypotensive effects, and ii) flosequinan; and b) introducing said flosequinan to said subject such that said symptoms are reduced. In another embodiment, said subject suffering from symptoms of a CNS disorder is being, or has been, treated with a drug that causes hypotensive effects.

In another embodiment, the method comprises a) providing: i) a subject (whether adult or child) suffering from symptoms of a CNS disorder who is not being treated (and/or has not been treated in the past) with a nitrite or nitrate, and ii) flosequinan; and b) introducing said flosequinan to said subject such that said symptoms are reduced. In another embodiment, said subject suffering from symptoms of a CNS disorder is being, or has been, treated with a nitrate or nitrite.

In yet other preferred embodiments, metabolites of cilostazol are contemplated for use in the methods of the presently claimed invention. Metabolites of cilostazol include, but are not limited to monohydroxcilostazol, monohydroxydehydrocilostazol, 3,4-dihydro-6-hydroxy-2 (1H)-quinolinone, their conjugates and dehydrocilostazol.

In one embodiment, the method comprises a) providing: i) a subject (whether adult or child) suffering from symptoms of a CNS disorder; and ii) cilostazol; and b) administering cilostazol to the subject (e.g. such that said symptoms are reduced). A variety of such symptoms are contemplated, including but not limited to, motor and vocal tics. In one embodiment, the present invention contemplates administering said composition to said adult or child under conditions such that frequency and/or severity of tics of said adult or child is diminished.

In one embodiment, the method comprises a) providing: i) a subject (whether adult or child) suffering from symptoms of a CNS disorder who is not being treated (and/or has not been treated in the past) with a drug that causes hypotensive effects, and ii) cilostazol; and b) introducing said cilostazol to said subject such that said symptoms are reduced. In another embodiment, said subject suffering from symptoms of a CNS disorder is being, or has been, treated with a drug that causes hypotensive effects.

In another embodiment, the method comprises a) providing: i) a subject (whether adult or child) suffering from symptoms of a CNS disorder who is not being treated (and/or has not been treated in the past) with a nitrite or nitrate, and ii) cilostazol; and b) introducing said cilostazol to said subject such that said symptoms are reduced. In another embodiment, said subject suffering from symptoms of a CNS disorder is being, or has been, treated with a nitrate or nitrite.

It is not intended that the present invention be limited to the mode of administration. In one embodiment, cilostazol is administered orally. In another embodiment, cilostazol is administered cutaneously. In yet another embodiment, cilostazol is administered intranasally. In an alternative embodiment, cilostazol is administered through respiratory inhalation. In yet another alternative embodiment, cilostazol is administered by standard injection (e.g intravenously or intramuscularly).

In a preferred embodiment, the male or female is an adult human and the oral dosage of cilostazol is in a single dose per day of up to approximately two hundred milligrams, and more preferably, between approximately ten to approximately one hundred milligrams. In an even more preferred embodiment, cilostazol is administered in two oral doses per day of between approximately fifty and approximately one hundred milligrams. In another preferred embodiment, the male or female is an adult human and the oral dosage of cilostazol is in three daily doses, before meals, each dose of up to approximately two hundred milligrams, and more preferably, between approximately ten to approximately seventy-five milligrams, and even more preferably, between approximately fifty to approximately one hundred milligrams.

It is not intended that the present invention be limited to the treatment of certain patient groups. In one embodiment, the patient is an adult. In another embodiment, the patient is a child. In one embodiment, the patient is free from cardiac diseases including, but not limited to, congestive heart failure. In another embodiment, the patient has not been treated with a drug that causes hypotensive effects. In yet another embodiment, the patient has not been treated with nitrates or nitrites.

In another embodiment, the method comprises providing: i) an adult or child with Tourette Syndrome, and ii) a pharmaceutical composition comprising cilostazol; and introducing the pharmaceutical composition to the adult or child (e.g. such that the symptoms of Tourette Syndrome of said adult or child are reduced).

It is not intended that the present invention be limited by the nature of the formulation. In one embodiment, the present invention contemplates a formulation comprising a quinolinone or derivative thereof in a mixture comprising lactose.

The present invention is not limited by the degree of response by the subject. It is expected that the administration of quinolinones will reduce symptoms of CNS disorders, including but not limited to, motor and vocal tics associated with Tourette Syndrome.

DEFINITIONS

Figure 1:
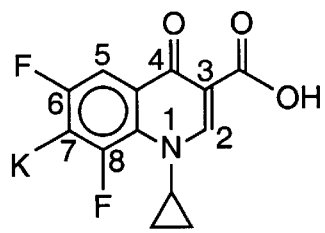
FIG. 1 depicts the chemical structure of a quinolinone (top) and 16 C-7 substituents (bottom).
Figure 1:
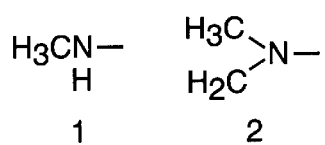
Figure 1:
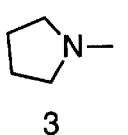
Figure 1:
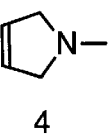
Figure 1:
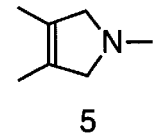
Figure 1:
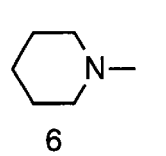
Figure 1:
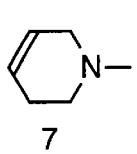
Figure 1:
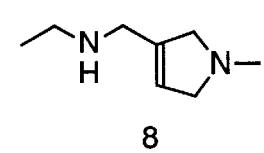
Figure 1:
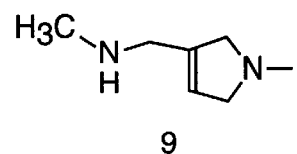
Figure 1:
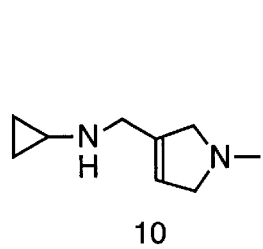
Figure 1:
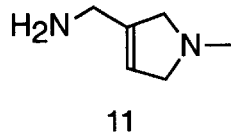
Figure 1:
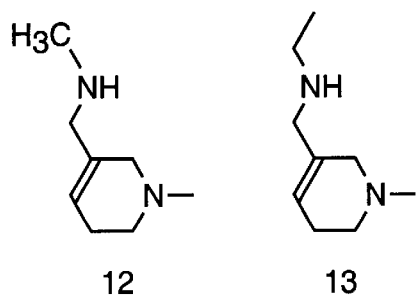
Figure 1:
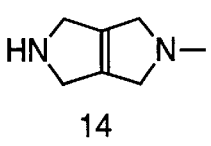
Figure 1:
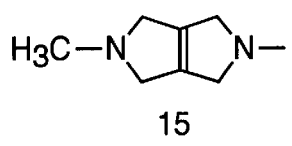
Figure 1:
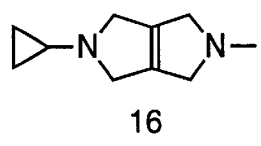

As used herein, the term "quinolinone" refers to chemical compositions comprising quinoline as set forth in the following structure (2-quinolone):

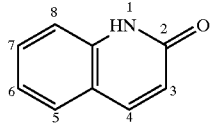

as well as other forms of quinolinone, (e.g., isoquinolone):

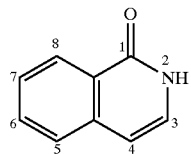

As used herein, the phrase "derivatives of quinolinone" refers to chemical compositions comprising quinolinone with a chemical group attached, including (but not limited to) halogenated quinolinone.

As used herein, the phrase "methylsulphinyl derivatives of quinolinone" refers to chemical compositions comprising quinolinone with a methylsulphinyl group attached. Examples include flosequinan (7-fluoro-1-methyl-3-(methylsulphinyl)-4(1H)-quinolone; 7-fluoro-1-methyl-3-(methylsufinyl)-4(1H)-quinolinone):

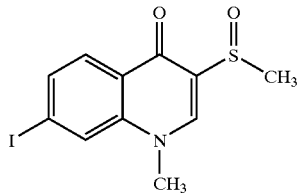

and sulfone metabolites of flosequinan:

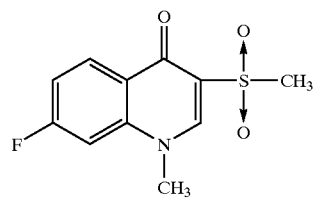

Other examples of quinolinone derivatives include cilostazol (6-[4-(1-cyclohexyl-1H-tetrazol-5-yl)butoxy]-3,4-dihydro-2(1H)-quinolinone; 6-[4-(1-cyclohexyl-1H-tetrazol-5-yl)butoxy]-3,4-dihydrocarbostyril; [3,4-Dihydro-6-(4-(1-cyclohexyl-1H-tetrazol-5-yl)butoxy)-2(1H)-quinolinone)]:

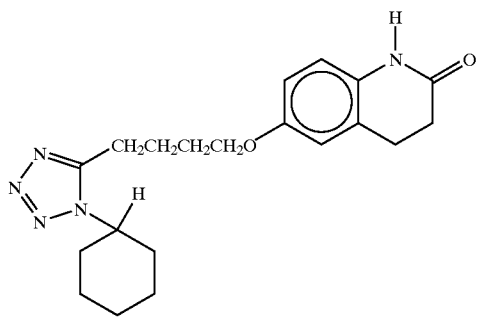

and metabolites of cilostazol. Examples include monohydroxycilostazol, monohydroxydehydrocilostazol, 3,4-dihydro-6-hydroxy-2(1 H)-quinolinone, their conjugates and dehydrocilostazol.

As used herein, "Central Nervous System disorder (CNS)" refers to any neurological disorder that affects the brain or spinal column, including, but not limited to Tourette Syndrome (TS), Parkinson's Disease, Huntington's Corea, Attention Deficit Hyperactivity Disorder (ADHD), Obsessive-Compulsive Disorder (OCD), Alzheimer's Disease, Tardive Dyskinesia (TD), Multiple Sclerosis (MS), depression, mania, and psychosis.

As used herein, the terms "lower alkyl", "lower alkoxy", "lower alkanoyl", and "lower alkythio" denote such groups containing 1–8 carbon atoms, especially 2–4 carbon atoms for lower alkanoyl and 1–4 carbon atoms for the other groups. Examples of such groups include methyl, ethyl, propyl, isopropyl, n-butyl, isobutyl, tert-butyl, n-heptyl, n-octyl, methoxy, ethoxy, propoxy, n-butoxy, isobutoxy, acetyl, propionyl, butyryl, methylthio, ethylthio, propylthio and n-butylthio.

As used herein, the term "active compound" denotes a pyridinone compound of general formula I (See "Other Compounds Useful in the Treatment of Central Nervous System Disorders" below), or a quinolinone or quinolinone derivative as illustrated and described above.

As used herein, "Tourette Syndrome" refers to an autosomal dominant neuropsychiatric disorder which affects the CNS and is characterized by a range of neurological and behavioral symptoms including, but not limited to, motor and vocal tics.

As used herein, "symptoms of Tourette Syndrome" refers to any two of the following symptoms: (A) the presence of both motor and vocal tics at some time during the illness, although not necessarily concurrently; (B) the occurrence of quasi-daily tics throughout a period of time exceeding one year; (C) variance in the clinical phenomenology of the tics; (D) marked distress or significant impairment in social, occupational, or other important areas of functioning; and (E) co-morbid symptoms such as Obsessive-Compulsive Disorder (OCD), Attention-Deficit Hyperactivity Disorder (ADHD), anxiety disorders, mood disorders, and panic disorders. Symptoms are "reduced" when the magnitude (e.g. intensity) or frequency of symptoms is reduced. It is not intended that the present invention be limited only to cases where the symptoms are eliminated. The present invention specifically contemplates treatment such that symptoms are reduced (and the condition of the patient is thereby "improved"), albeit not completely eliminated.

As used herein, a patient who is "free from cardiac disease" and a patient who is "free from symptoms of cardiac disease" indicate that the patient has not been diagnosed with angina, myocardial infarction, congestive heart failure and that symptoms of angina, ischemia, myocardial infarction, and/or congestive heart failure have not been detected.

As used herein, "drugs that have hypotensive effects" are those drugs which, when administered, cause the patient's end-diastolic blood pressure to be reduced. Nitrates are commonly used drugs which have hypotensive effects.

As used herein, "nitrates" are compounds that contain the —$NO_3$— moiety. Nitrates typically used in the clinic are shown in Table 1.

As used herein, "nitrites" are compounds that contain the —$NO_2$—moiety. Nitrites typically used in the clinic are shown in Table 1. As used herein "standard injection" refers to the placement of a pharmaceutical composition into a subject (e.g., with a hypodermic needle). For example, such injection can be made subcutaneously, intravenously, intramuscularly, intrathecally, etc.

As used herein, "by oral administration" refers to the introduction of a pharmaceutical composition into a subject by way of the oral cavity (e.g., in aqueous liquid or solid form).

As used herein, "cutaneously" refers to the introduction of a pharmaceutical composition into a subject by application to the surface of the skin such that the composition is absorbed into the subject.

As used herein, "intranasally" refers to the introduction of a pharmaceutical composition within the nasal cavity.

As used herein, "respiratory inhalation" refers to the introduction of a pharmaceutical composition within the respiratory tract.

As used herein "single dosage" refers to a pharmaceutical composition of a formulation that is capable of achieving its intended effect in a single administration or application.

As used herein, the term "subject" refers to both humans and animals.

As used herein, the term "enantiomer" refers to stereoisomers of molecules that are non-superimposable mirror images of each other. Enantiomers have identical physical properties, such as melting points and boiling points, and also have identical spectroscopic properties. Enantiomers differ from each other with respect to their interaction with plane-polarized light, and with respect to biological activity.

As used herein, the term "stereoisomer" refers to compounds that have their atoms connected in the same order but differ in the arrangement of their atoms in space. (e.g. cis-2-butane and trans-2-butane).

TABLE 1

| NONPROPRIETARY NAMES AND TRADE NAMES | CHEMICAL STRUCTURE | PREPARATIONS, USUAL DOSES, AND ROUTES OF ADMINISTRATION* |
|---|---|---|
| Amyl nitrite (isoamyl nitrite) | 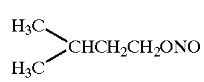 | Inh: 0.18 or 0.3 ml, inhalation |
| Nitroglycerin (glyceryl trinitrate; NITRO-BID, NITROSTAT, NITROL, NITRO-DUR, others) | 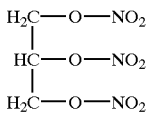 | T: 0.15 to 0.6 mg as needed<br>S: 0.4 mg per spray as needed<br>C: 2.5 to 9 mg two to four times daily<br>B: 1 mg every 3 to 5 h<br>O: 1.25 to 5 cm (½ to 2 in.), topically to skin every 4 to 8 h<br>D: 1 disc (2.5 to 15 mg) every 24 h<br>IV: 5 μg/min; increments of 5 μg/min |
| Isosorbide dinitrate (ISORDIL, SORBITRATE, DILATRATE, others) | 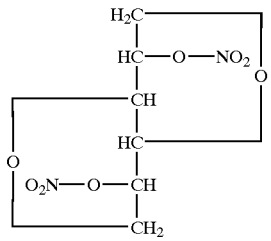 | T: 2.5 to 10 mg every 2 to 3 h<br>T(C): 5 to 10 mg every 2 to 3 h<br>T(O): 10 to 40 mg every 6 h<br>C: 40 to 80 mg every 8 to 12 h |

TABLE 1-continued

| NONPROPRIETARY NAMES AND TRADE NAMES | CHEMICAL STRUCTURE | PREPARATIONS, USUAL DOSES, AND ROUTES OF ADMINISTRATION* |
| --- | --- | --- |
| Isosorbide-5-mononitrate (IMDUR, ISMO, others) | [structure of isosorbide-5-mononitrate] | T: 10 to 40 mg twice daily<br>C: 60 mg daily |
| Erythrityl tetranitrate (CARDILATE) | $H_2C-O-NO_2$<br>$HC-O-NO_2$<br>$HC-O-NO_2$<br>$H_2C-O-NO_2$ | T: 5 to 10 mg as needed<br>T(O): 10 mg three times daily |

*buccal (transmucosal) tablet; C, sustained-release capsule or tablet; D, transdermal disc; Inh, inhalant; IV, intravenous injection; O, ointment; S, lingual spray; T, tablet for sublingual use; T(C), chewable tablet; T(O), oral tablet or capsule.

As used herein, the term "diastereoisomers" refers to stereoisomers that are not mirror images of each other.

As used herein, the terms "purified enantiomer" and "purified enantiomer preparation" are meant to indicate a preparation (e.g. derived from the racemic mixture) wherein one enantiomer represents less than 10%, and more preferably less than 5%, and still more preferably, less than 2% of the preparation.

As used herein, the term "racemic mixture" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

DETAILED DESCRIPTION OF THE INVENTION

The present invention provides relates to methods and compositions for the treatment of Central Nervous System disorders in adults and children (including but not limited to Tourette Syndrome) in particular treatment groups. The methods of the present invention comprise the utilization of pharmaceutical compositions to patients who are free of symptoms of cardiac disease and who have not been treated with drugs which cause hypotensive effects, such as nitrites and nitrates. The compositions comprise quinolinones, including derivatives and enantiomers thereof. A variety of quinolinone derivatives are shown in FIG. 1. Methods for producing antibiotic derivatives of a particular quinolone carboxylic acid skeleton are provided in U.S. Pat. No. 4,623,650 to Gilligan et al., hereby incorporated by reference.

In one embodiment, racemic flosequinan or an enantiomer of flosequinan is administered. Importantly, flosequinan may potentiate the hypotensive effects of nitrates, and its administration to patients who are concurrently using organic nitrates in any form may be contraindicated.

In one embodiment, the present invention contemplates the use of compositions that are effective to control the symptomatic motor and vocal tics suffered by adults and children with Tourette Syndrome. The compositions comprise a quinolinone, including derivatives and enantiomers thereof.

While the present invention is not limited by the nature of the derivatives, in one embodiment, the present invention encompasses the use of a variety of quinolinone derivatives (e.g., 5-bromoquinoline, 5-nitroisoquinoline, 8-nitroisoquinoline and 1-methylisoquinoline). One skilled in the art can readily produce such derivatives as set forth in McMurry, Organic Chemistry, 2nd Ed., Brooks/Cole Publishing, Belmont, Calif. (1988), pages 1044–1045 and 1076.

In another embodiment, the present invention contemplates the use of methylthio and methylsulphinyl derivatives of quinolinone. In a preferred embodiment, the methylsulphinyl derivative is flosequinan (whether as a racemic mixture or as a purified enantiomer).

Flosequinan

Methods of producing methylsuphinyl and methylthio derivatives of quinolinone, including flosequinan, are set forth in U.S. Pat. Nos. 5,079,264 and 5,011,931 to MacLean et al., hereby incorporated by reference. While it is not necessary to understand any particular mechanism to carry out the present invention, it is believed that in some circumstances flosequinan can act to diminish the symptoms of CNS disorders, including but not limited to, the symptoms associated with Tourette's Syndrome.

The action of flosequinan in the body is not precisely understood. Its activity in the body is attributed to flosequinan itself, as well as its sulfone metabolite. It has been reported to be useful to some degree in the treatment of heart failure. (See Kelso et al., *J. Cardiovasc. Pharmacol.* 25: 376 (1995)). However, its action appears to have little effect in patients with end-stage failure [Perreault et al., *Br. J. Pharmacol.* 106: 511 (1992)] and does not affect mortality or arrhythmias following coronary artery ligation. (See Jones et al., *Br. J. Pharmacol.* 108: 1111 (1993)).

Likewise, flosequinan has been reported to be a selective inhibitor of phosphodiesterase III. (See Gristwood et al., *Br. J. Pharmacol.* 105: 985 (1992) and Frodsham et al., *Eur. J. Pharmacol.* 211: 383 (1992); See also, Examples 2 & 3).

However, report that the phosphodiesterase inhibition of flosequinan, as relevant to its efficacy in heart failure, is questionable. Thus, the application of flosequinan to particular purposes in the body is not well-characterized and must be determined empirically.

In another embodiment, the present invention contemplates the use of purified enantiomers of flosequinan. Although the present invention is not limited by a specific means of producing enantiomers of flosequinan, methods of producing a racemic mixture of flosequinan, are set forth in U.S. Pat. Nos. 5,079,264 and 5,011,931 to MacLean et al., hereby incorporated by reference. Moreover, a means of resolving the enantiomers of flosequinan is set forth in Morita et al., "Synthesis and Absolute Configuration of the Enantiomers of 7-Fluoro-1-methyl-3-(methylsulfinyl)-4 (1H)-quinolinone (Flosequinan)," Chem. Pharm. Bull., 42(10): 2157–2160 (1994), hereby incorporated by reference.

Resolution of the (+) and (−) Enantiomers of Flosequinan

The present invention contemplates the resolution of the (+) and (−) enantiomers of flosequinan. Many organic compounds, including flosequinan, exist in optically active forms (i.e., they have the ability to rotate the plane of plane-polarized light). In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory (rotates to the left). A compound prefixed with (+) or d is dextrorotatory (rotates to the right). For a given chemical structure, these compounds, called "stereoisomers," are identical except that they are mirror images of one another.

Stereochemical purity is of importance in the field of pharmaceuticals, where 12 of the 20 most prescribed drugs exhibit chirality. A case in point is provided by the L-form of the beta-adrenergic blocking agent, propranolol, which is known to be 100 times more potent than the D-enantiomer. Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been believed to be a potent teratogen.

The present invention is not limited by any specific means of resolving the (+) and (−) enantiomers of flosequinan to obtain a purified enantiomer of flosequinan. In one embodiment, said enantiomers are resolved as follows. A racemic mixture of flosequinan is subjected to high-performance liquid chromatography (HPLC) over a Chiracel OD column (Chiral Technologies, Exton, Pa.) at a flow rate of 1.0 ml/minute. A mobile phase comprising methanol is utilized, resulting in the resolution of a distinct peak for each enantiomer. The resolved (+) and (−) enantiomers of flosequinan are eluted with methanol with an optical purity greater than 99%.

Cilostazol

In another embodiment, the compositions utilized in the methods of the present invention comprise cilostazol, including derivatives thereof. Cilostazol is a phosphodiesterase inhibitor (type III) that suppresses platelet aggregation and also acts as a direct arterial vasodilator. In addition to its reported vasodilator and antiplatelet effects, cilostazol has been proposed to have beneficial effects on plasma lipoproteins, increasing plasma high density lipoprotein cholesterol and apoliproprotein (See e.g., Dawson et al., Circulation 98: 678–686 (1998); Elam et al., Arterioscler Thromb. Vasc. Biol. 18: 1942–1947 (1998); Drug Evaluation Monographs, vol. 99, Micromedex Inc.).

Method of preparation of cilostazol are set forth by Nishi et al., Chem. Pharm. Bull. 31: 1151 (1983), and U.S. Pat. No. 4,277,479, hereby incorporated by reference), and its pharmacology, metabolism, mechanism of action and clinical evaluations are described in Arzneimittel-Forsch. 35: 1117–1208 (1985), hereby incorporated by reference. While it is not necessary to understand any particular mechanism to carry out the present invention, it is believed that in some circumstances cilostazol can act to diminish the symptoms of CNS disorders, including but not limited to, the symptoms associated with Tourette's Syndrome.

In one embodiment cilostazol is administered. It is contemplated that cilostazol be administered cutaneously, by standard injection, intranasally, or through respiratory inhalation, although it is not intended that the methods of the present invention be limited to the mode of administration of cilostazol. In one embodiment, cilostazol is administered as a tablet. In another embodiment, cilostazol is administered as a pharmaceutical composition.

While the present invention is not limited to the treatment of a particular patient group, it is contemplated that the methods of the present invention comprise the utilization of pharmaceutical compounds and compositions to patients who are free of symptoms of cardiac disease and who have not been treated with drugs which cause hypotensive effects, such as nitrites and nitrates.

Diagnosis of Tourette Syndrome (TS)

Determination whether a human adult or child is suffering from Tourette Syndrome is readily made by a person skilled in the art using a number of readily available diagnostic procedures and is based on the presence of symptoms associated with the disease. The prevailing diagnostic criteria for TS recommended by the American Psychiatric Association include both multiple motor and vocal tics over a period of more than one year, voluntary suppression of symptoms, a waxing and waning course, and onset between ages two and twenty-one years. (See also, Robertson M., "Tourette Syndrome, associated conditions and the complexities of treatment," Brain, 123: 425, 427 (2000)).

As well as tics, there are a variety of behavioral and psychological difficulties that are experienced by many, though not all, patients with TS. The most frequently reported behavioral problems are attention deficits, obsessions, compulsions, impulsivity, irritability, aggressivity, immaturity, self-injurious behaviors, and depression. Some of the behaviors (e.g. obsessive-compulsive behavior) may be an integral part of TS, while others may be more common in TS patients because of certain biological vulnerabilities (e.g. ADHD). Still others may represent responses to the social stresses associated with a multiple tic disorder or a combination of biological and psychological reactions.

A neurological examination of a patient diagnosed with TS should include documentation of neuromaturational difficulties and other neurological findings. About half of TS patients have non-localizing neurological findings suggesting disturbances in the body scheme and integration of motor control. Such findings are worth noting as "baseline" data since the use of medications such as haloperidol may cloud the neurological picture.

Additional studies that may be considered in the biological work-up include serum electrolytes, calcium, phosphorous, copper, ceruloplasmin, and liver function tests—all related to movement disorders of various types. However, in practice, such tests are rarely needed for a diagnosis.

Finally, previous medications taken by the patient must be reviewed in detail during a clinical assessment of a patient diagnosed with TS. For example, if a child has received stimulant medications, it is important to determine for what indications the medications were administered, whether there were any pre-existing tics or compulsions, and the temporal relation between the stimulants and the new symptoms. Catecholaminergic agonists are contained in other drugs, such as in decongestant combinations used in treating allergies and in medications used for asthma. If a patient with TS is taking a stimulant or a drug containing an ephedrine-like agent, discontinuation should be strongly considered.

Treatment of Tourette Syndrome

It is not intended that the present invention be limited by the particular nature of the therapeutic preparation. For example, the quinolinones (e.g. cilostazol) or quinolinone derivatives (e.g., flosequinan) can be provided together with physiologically tolerable liquid, gel or solid carriers, diluents, adjuvants and excipients. In addition, quinolinone analogs may be used together with other chemotherapeutic agents. On the other hand, formulations may also contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The present invention is not limited by the method of introduction of the therapeutic compound to the body. Among other methods, the present invention contemplates administering cutaneously, orally, or by standard injection (e.g. intravenous).

The present invention also contemplates administering flosequinan or cilostazol to the patient intranasally or through respiratory inhalation. Formulations suitable for intranasal administration include ointments, creams, lotions, pastes, gels, sprays, aerosols, oils and other pharmaceutical carriers which accomplish direct contact between flosequinan, cilostazol, or a pharmaceutical composition comprising flosequinan or cilostazol and the nasal cavity. Examples of pharmaceutical compositions administered intranasally are described in U.S. Pat. Nos. 5,393,773 and 5,554,639 to Craig et al.; and U.S. Pat. No. 5,801,161 to Merkus, all hereby incorporated by reference. Formulations suitable for respiratory inhalation include ointments, creams, lotions, pastes, gels, sprays, aerosols, oils and other pharmaceutical carriers which accomplish direct contact between flosequinan, cilostazol, or a pharmaceutical composition comprising flosequinan or cilostazol and the respiratory tract. Examples of pharmaceutical compositions administered through respiratory inhalation are described in U.S. Pat. No. 4,552,891 to Hu et al.; U.S. Pat. No. 5,869,479 to Kreutner et al., and U.S. Pat. No. 5,864,037 to Chasis et al., all hereby incorporated by reference.

In some embodiments, intranasal administration and respiratory inhalation are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacologic agents to patients can be accomplished via aerosolization. Alternatively, the agent may be administered to the lung through a bronchoscope. Of course, the therapeutic agents may be investigated for their efficacy via other routes of administration, including parenteral administration.

Oral administration of flosequinan is an effective mode of administration, with a mean absolute bioavailability of 72% following a single does of fifty milligrams. Peak plasma concentrations of flosequinan are observed 1–2 hours following oral administration, while peak metabolite plasma levels are observed about seven hours following oral dosage. While the present invention is not limited to a specific dosage level, for adult humans, in one preferred embodiment the dosage is a single dosage per day of 25 milligrams, while in another preferred embodiment the dosage is a single dosage per day of 50 milligrams, while in yet another preferred embodiment the dosage is a single dosage per day of 75 milligrams. In another preferred embodiment, the dosage is a single dosage per day of approximately 125 milligrams and in another preferred embodiment, the dosage is a single dosage per day of approximately 150 milligrams. In another preferred embodiment, the per day dosage is a single dosage of approximately 200 milligrams. Multiple dosages are also contemplated by the invention.

Flosequinan is water soluble and is soluble in many organic solvents. Thus, while the present invention is not limited by the form of oral administration, aqueous and organic solution of flosequinan for oral administration is contemplated. Likewise, flosequinan can be associated with a solid pharmaceutical carrier for solid oral administration (i.e., in pill form). One skilled in the art is able to readily prepare such solid formulations, and in one embodiment, the inactive ingredients include croscarmellose sodium, hydroxypropyl methylcellulose, lactose, magnesium stearate, methocel E5, microcrystalline cellulose, povidine, propylene glycol and titanium dioxide.

The oral administration of cilostazol is possible. While the present invention is not limited to a specific dosage level, a single dosage per day of up to approximately 200 milligrams, and more preferably, between approximately ten to approximately one hundred milligrams, is contemplated. In another embodiment, a dosage of less than 100 milligrams of cilostazol per day is contemplated (i.e., 25–75 milligrams per day). Multiple dosages are also contemplated. In a preferred embodiment, two dosages per day of approximately 50 to approximately 100 milligrams of cilostazol are contemplated. In an even more preferred embodiment, cilostazol is administered in two oral doses per day of between approximately fifty and approximately one hundred milligrams. In another preferred embodiment, the male or female is an adult human and the oral dosage of cilostazol is in three daily doses, before meals, each dose of up to approximately two hundred milligrams, and more preferably, between approximately ten to approximately seventy-five milligrams, and even more preferably, between approximately fifty to approximately one hundred milligrams.of cilostazol for adult humans is contemplated. Peak plasma concentrations of cilostazol are observed 2–4 hours following oral administration (See e.g., Suri et al., *J. Clin. Pharmacol.* 38: 144–150 (1998); Niki and Mori, Arzneimittelforschung 35: 1173–1185 (1985)).

While the present invention is not limited by the form of oral administration, aqueous and organic solutions of cilostazol for oral administration are contemplated. Likewise, cilostazol can be associated with a solid pharmaceutical carrier for solid oral administration. The compositions may be formulated in a manner known to one skilled in the art, using pharmaceutically acceptable carriers suitable for use in such compositions that are also well known in the art. It is contemplated that the compositions of the present invention comprise 0.1–90% by weight of cilostazol. In one embodiment, cilostazol can be prepared in tablet form by mixing cilostazol with an inert diluent such as lactose (See e.g., U.S. Pat. No. 5,627,191 to Birch et al., hereby incorporated by reference). In one preferred embodiment, cilostazol is administered as a tablet.

Flosequinan and cilostazol may also be administered cutaneously in a carrier adapted for topical administration. Such carriers include creams, ointments, lotions, pastes, jellies, sprays, aerosols, bath oils, or other pharmaceutical carriers which accomplish direct contact between flosequinan, or cilostazol, and the pore of the skin. In general pharmaceutical preparations may comprise from about 0.001% to about 10%, and preferably from about 0.01 to 5% by w/w of the active compound (e.g., flosequinan) in a suitable carrier. In some cases it may be necessary to dissolve the flosequinan in an appropriate solvent such as ethanol or DMSO (dimethylsulfoxide), and the like, to facilitate incorporation into a pharmaceutical preparation.

Flosequinan and cilostazol may also be administered by any standard injection means (e.g., employing an hypodermic syringe and needle or a similar device such as the NovolinPen. sold by Squibb-Novo, Inc., Princeton, N.J., USA). This injection may be accomplished by a subject injecting him or herself, or by the injection of the subject by another person. Standard injection may be administered to the subject, including but not limited to, intravenously, intramuscularly, or intrathecally.

Flosequinan and cilostazol can be introduced by injection in a physiologically acceptable composition. Such compositions are aqueous solutions that are physiologically acceptable for administration by any standard injection means. The physiologically acceptable carrier is selected such that it is not painful or irritating upon injection. The physiologically acceptable compositions will preferably be sterile at the time of administration by injection.

Among the physiologically acceptable compositions for use in the methods is physiological saline or phosphate-buffered saline, in which flosequinan or cilostazol is dissolved or suspended, such that the resulting composition is suitable for standard injection. Such a physiologically acceptable composition can also include a non-irritant preservative, such as, e.g., benzalkonium chloride at 0.05% (w/v) to 0./2% (w/v). As the skilled artisan will understand, there are numerous non-toxic salts of VIP, PHM and α-adrenergic blockers that can be employed in a physiologically acceptable composition for use in the methods herein, including, among others, the chloride, bromide, acetate, sulfate, and mesylate salts.

While the present invention is not limited to the method of injecting flosequinan or cilostazol, in the preferred embodiment, it is injected with a standard syringe. One skilled in the art would be capable of injecting flosequinan or cilostazol with a carrier as described for conventional injection.

The present invention is not limited by the degree of response by the subject. It is expected that the administration of quinolinones will reduce symptoms of CNS disorders, including but not limited to, motor and vocal tics associated with Tourette syndrome. It is also expected that the administration of quinolinones for treatment of CNS disorders will not result in the side effect of impotence as is seen in the administration of neuroleptics, anti-obsessives, and anti-depressants.

From the above, it should be clear that the present invention provides methods of treatment of CNS disorders with pharmaceutical agents. In particular, quinolinones are administered therapeutically to patients having such a disorder.

All publications and patents mentioned in the above specification are herein incorporated by reference. Various modifications and variations of the described method and system of invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

Other Compounds Useful in the Treatment of Central Nervous System Disorders

The invention is further directed to pyridinone compounds with therapeutic activity, and to therapeutic compositions containing such compounds, wherein the compounds have the general formula I:

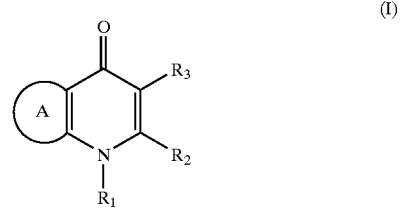

(I)

$R_1$ is hydrogen, lower alkyl optionally substituted by hydroxy or $C_{1-4}$ alkoxycarbonyl, allyl, propynyl or phenyl-lower alkyl in which the phenyl ring is optionally substituted by 1 or 2 $C_{1-4}$ alkoxy groups;

$R_2$ is hydrogen or lower alkyl;

$R_3$ is $(X)_m$—$S(O)_nR_4$, $COR_5$, $SR_6$, or $S(OH)(O)NR_7$, wherein m is 0 or 1, n is 0, 1, or 2, X is oxygen or lower alkylene, $R_4$ is $C_{1-4}$ alkyl, $R_5$ is hydroxyl, lower alkyl carbonyl, amino, or lower alkyl amino, and $R_6$ and $R_7$ are lower alkyl; and ring A represents an optionally substituted phenyl ring of the formula:

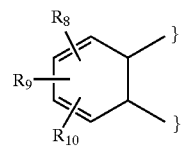

wherein $R_8$, $R_9$, and $R_{10}$, which may be the same or different, are hydrogen, lower alkyl, lower alkoxy, lower alkanoyl, halo, tri-fluoromethyl, lower alkylthio, lower alkylsulphinyl, lower alkylsulphonyl, halogenated lower alkyl, halogenated lower alkoxy, cyano, phenyl, or phenyl substituted by 1 to 3 groups independently selected from lower alkyl, lower alkoxy and trifluoromethyl; or ring A represents an optionally substituted thiophene ring of the formula:

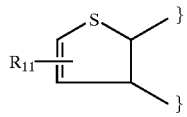

wherein $R_{11}$ is hydrogen, lower alkyl, lower alkoxy, lower alkanoyl, halo, trifluoromethyl, lower alkylthio, phenyl, or phenyl substituted by halogen, or a pharmaceutically acceptable salt thereof.

The compounds of the general formula I have been found to have antihypertensive activity and cardiac activity in warm-blooded animals. The compounds, methods of making the compounds, antihypertensive and cardiac therapeutic compositions of the compounds, and methods for treating hypertension and heart failure using the compounds are described in U.S. Pat. Nos. 4,302,460, 4,522,884, 4,855,291, 4,877,793, 4,710,506, 4,772,614 and 4,997,840, the disclosures of which patents are expressly incorporated herein, in their entirety, by reference.

In a preferred embodiment, the invention provides pharmaceutical compositions comprising compounds of the general formula I, and methods of using the compositions to treat subjects with symptoms of a central nervous system disorder, such that said symptoms are reduced. As described above for flosequinan and cilostazol, the invention is not limited by the particular nature of the pharmaceutical composition, or by the method of introduction of the active or therapeutic compound to the body. All of the treatment methods and compositions contemplated above are also contemplated here for compounds of formula I. The active ingredient in the compositions is preferably administered in unit dosage form. In one embodiment, tablets and capsules may conveniently contain a unit dosage of the active compound of 1–500 mg/kg, more preferably 5–100 mg/kg and still more preferably 5–50 mg/kg.

The compounds of formula I may contain one or more asymmetric centers and, therefore, can exist as enantiomers or diastereoisomers. Furthermore, certain compounds of formula I containing alkenyl groups may exist as cis-isomers or trans-isomers. In each case, the invention includes both mixtures and separate individual isomers. The compounds of formula I may also exist in tautomeric forms and the invention includes both mixtures and separate individual tautomers.

Preferred compounds of the general formula I for use in the pharmaceutical compositions and methods of the invention are compounds having the general formulas II and III:

(II)

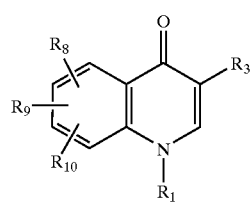

(III)

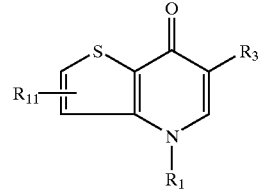

wherein $R_1$, $R_3$, $R_8$, $R_9$, $R_{10}$, and $R_{11}$ are defined as above.

With regard to compounds of formula II, still more preferred compounds have the formula IIA:

(IIA)

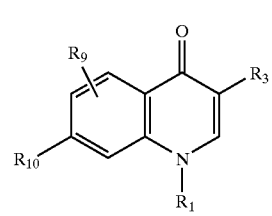

wherein $R_3$ is $(X)_m$—$S(O)_n R_4$, $COR_5$, $SR_6$, or $S(OH)(O)NR_7$; and (a) $R_{10}$ is hydrogen and $R_9$ is 6-lower alkoxy, 8-lower alkoxy, 5-halo or 6-halo;

(b) $R_9$ is hydrogen and $R_{10}$ is halo; lower alkyl, lower alkoxy, trifluoromethyl or lower alkyl-thio;

(c) $R_{10}$ is halo, lower alkoxy or lower alkyl and $R_9$ is 6-lower alkyl, 6-lower alkoxy or 6-halo of a different value from $R_{10}$; or (d) $R_9$ and $R_{10}$ are hydrogen.

Preferred embodiments include compounds of formula IIA wherein $R_1$ and $R_2$ are methyl, $R_9$ is hydrogen and $R_{10}$ is halo, lower alkyl or trifluoromethyl. More preferably, $R_{10}$ is halo or $C_1$–$C_4$ alkyl. In yet another preferred embodiment, $R_9$ is 6-lower alkoxy and $R_{10}$ is halo or lower alkoxy. In a further preferred embodiment, $R_9$ is 6-halo and $R_{10}$ is lower alkoxy. In another preferred embodiment, $R_{10}$ is $C_1$–$C_4$ alkyl. Thus, preferred embodiments include compounds of formula IIB, IIC, IID, IIE, IIF, IIIA and IIIB as follows:

(IIB)

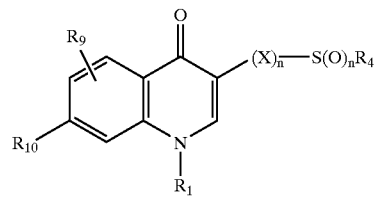

(IIC)

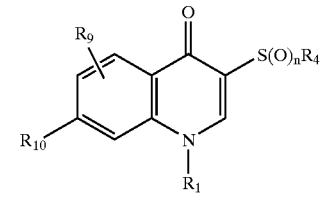

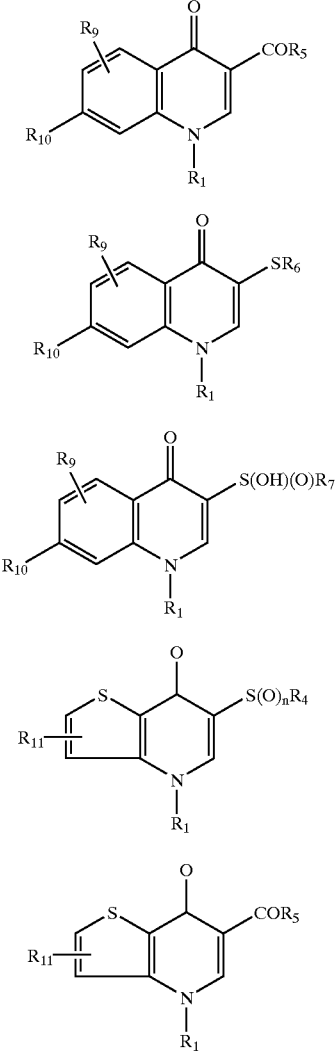

Preferred compounds of formula IIB are those in which m is 1, n is 2, and X is oxygen. Preferred compounds of formula IIC include those in which m is 0, n is 1 or 2, and $R_4$ is methyl. Preferred compounds of formula IID include those in which $R_5$ is amino or lower alkyl amino. Preferred compounds of formula IIE include those in which $R_6$ is methyl. Preferred compounds of formula IIF include those in which $R_7$ is methyl. Preferred compounds of formula IIIA include those in which n is 1 and $R_4$ is methyl. Preferred compounds of formula IIIB include those in which $R_5$ is amino or lower alkyl amino.

Specific preferred compounds of these formulae include: 1-methyl-3-methylsulphinyl-4-quinolone, 7-fluoro-1-methyl-4-oxo-1,4-dihydro-quinolone-3-carboxamide, 4-methyl-7-oxo-4,7-dihydrothieno[3,2-b]pyridine-6-carboxamide, 4-methyl-6-methylsulphinyl-7(4H)-thieno[3,2-b]pyridinone, 7-chloro-1-methyl-3-methylsulphamoyl-4-quinolone, 1-methyl-4-oxo-1,4-dihydroquinol-3-yl methanesulphonate, 7-chloro-1-methyl-4-oxo-1,4-dihydroquinoline-3-carboxamide, 7-fluoro-1-methyl-3-methylsulphonyl-4-quinolone, or 7-fluoro-1-methyl-3-methylthio-4-quinolone, or pharmaceutically acceptable salts thereof.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); L (liters); ml (milliliters); $\mu$l (microliters); cm (centimeters); mm (millimeters); $\mu$m (micrometers); nm (nanometers); °C. (degrees Centigrade).

EXAMPLE 1

Production and Purification of Enantiomers of Flosequinan

Figure 2:
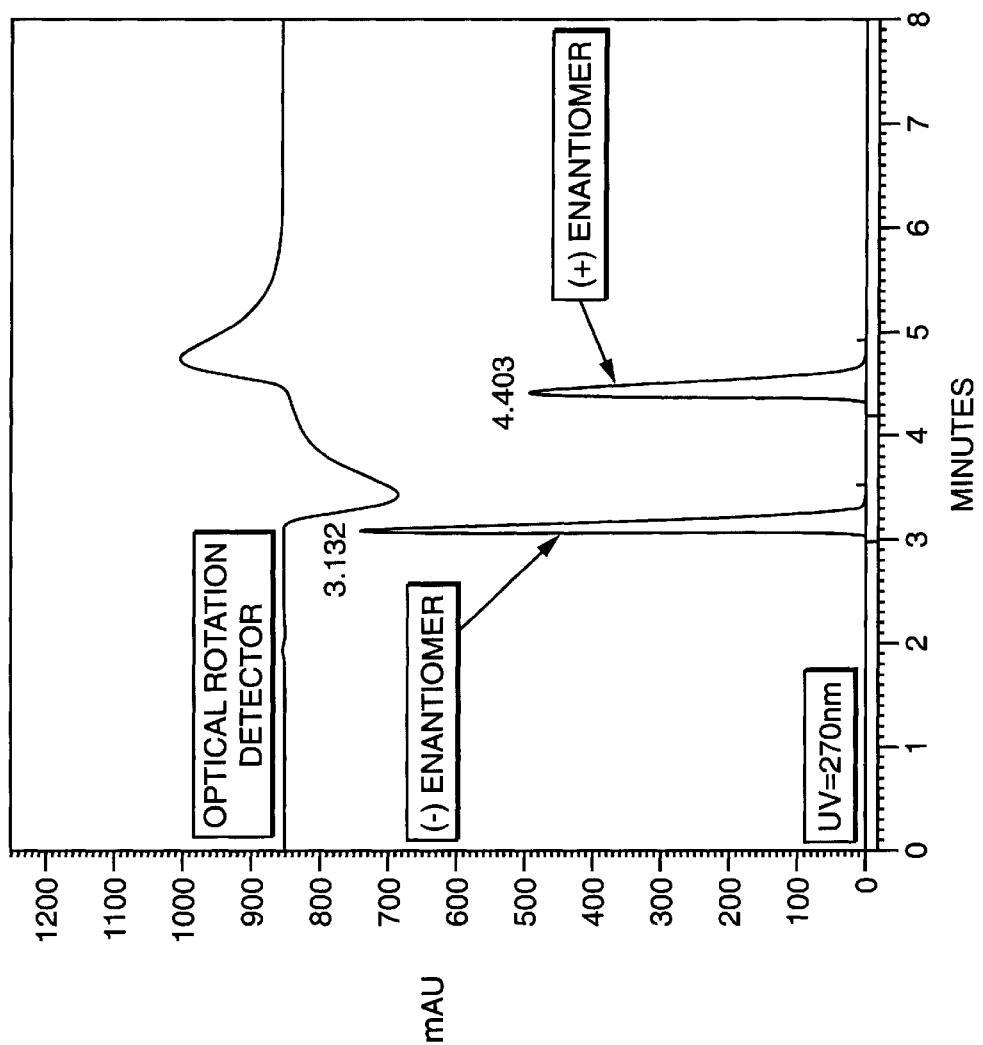
FIG. 2 depicts the respective HPLC column retention times and optical rotations of the enantiomers of flosequinan separated by the method provided in Example 1.

In this example, the enantiomers of flosequinan were resolved by high-performance liquid chromatography (HPLC) as follows. A 5.0 g sample of a racemic mixture of flosequinan was resolved over a 10 cm ID×50 cm L CHIRALCEL OD HPLC column (Chiral Technologies, Exton, Pa.) at 25° C. and with a flow rate of 1.0 ml/minute such that the column pressure was 37 bar. The mobile phase employed was 100% methanol and the detection of the mixture was performed at 270 nm. The (−) enantiomer had a retention time of 3.13 minutes, while the (+) enantiomer had a retention time of 4.40 minutes. A total of 2.1 g of the (−) enantiomer having an optical purity greater than 99% was produced. A total of 2.3 g of the (+) enantiomer having an optical purity greater than 99% was produced. (See, FIG. 2).

EXAMPLE 2

Sildenafil citrate (Viagra) has been suggested as a pharmacological treatment for Tourette Syndrome. However, sidenafil citrate has a lack of specificity for its target, enzyme phosphodiesterase 5 (PDE5), and exerts a definite inhibition on the enzyme phosphodiesterase 6 (PDE6), located in the retina. It has been shown that the inhibition of PDE6 results in color vision defects as a side effect of treatment with sildenafil citrate. Furthermore, side effects such as flushing, headache, nasal congestion, and dyspepsia (heartburn) have also been associated with sildenafil citrate treatment of impotence. (See, Moreira et al., "Side-effect profile of sildenafil citrate (Viagra) in clinical practice," *Urology*, 56(3): 474–76 (2000)). In this example, a biochemical assay was performed to test the percentage of phosphodiesterase 6 (PDE6) inhibition of various molar concentrations of sildenafil citrate (Viagra) as compared to that of a 100 $\mu$M concentration of a racemic mixture of flosequinan as follows. (See also Example 3).

PDE6 partially purified from bovine retinal rod and activated by trypsin was used. In four separate reactions, Viagra at molar concentrations of 0.3 $\mu$M, 1.0 $\mu$M, and 3.0 $\mu$M, and a 100 $\mu$M racemic mixture of flosequinan were incubated with 0.2 $\mu$g/ml active PDE6 and 100 $\mu$M cGMP containing 0.1 $\mu$M [$^3$H]cGMP in Tris buffer pH 7.5 for 20 minutes at 30° C. Each reaction was terminated by raising the temperature to 100° C. for 2 minutes. The resulting GMP was converted to guanosine by addition of 10 mg/ml snake venom nucleotidase and further incubated at 30° C. for 10 minutes. Unhydrolyzed cGMP was bound to AGI-X2 resin, and [$^3$H]guanosine remaining in the aqueous phase was quantitated by scintillation counting.

The results of the assays, as noted in the table below, indicate that although Viagra inhibits PDE6 around 50% at concentrations as low as 0.3 $\mu$M, such levels of inhibition of PDE6 require greater than 100 $\mu$M amounts of flosequinan (i.e. more than 300 times more compound on a molar basis). These empirical results could not be predicted.

| Compound | Concentration | % Inhibition of PDE6 |
|---|---|---|
| Viagra | 3.0 $\mu$M | 87 |
| Viagra | 1.0 $\mu$M | 62 |
| Viagra | 0.3 $\mu$M | 57 |
| Flosequinan | 100 $\mu$M | 36 |

EXAMPLE 3

In this example, a racemic mixture of flosequinan and the (+) and (−) enantiomers of flosequinan were subjected to biochemical enzyme assays to determine their respective percent inhibition of a variety of phosphodiesterases (PDE1–PDE6). The reaction conditions for each PDE assay were as follows.

PDE1: PDE1 partially purified from bovine heart was used. A racemic mixture of flosequinan, and each enantiomer of flosequinan, all at a molar concentration of 100 $\mu$M, were independently incubated with 13 $\mu$g PDE1 enzyme, 1.0 $\mu$M [$^3$H]cAMP and CaCl$_2$/calmodulin in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE2: PDE2 partially purified from human platelets was used. A racemic mixture of flosequinan, and each enantiomer of flosequinan, all at a molar concentration of 100 $\mu$M, were independently incubated with 23 $\mu$g PDE2 enzyme, 25 $\mu$M cAMP containing 0.05 $\mu$M [$^3$H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE3: PDE3 partially purified from human platelets was used. A racemic mixture of flosequinan, and each enantiomer of flosequinan, all at a molar concentration of 100 $\mu$M, were independently incubated with 13 $\mu$g PDE3 enzyme and 1 $\mu$M cAMP containing 0.01 $\mu$M [$^3$H]cAMP in Tris buffer pH 7.5 for 20 minutes at 30° C. The reaction was terminated by boiling for 2 minutes, and the. resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE4: PDE4 partially purified from human U-937 pronocytic cells was used. A racemic mixture of flosequinan, and each enantiomer of flosequinan, all at a molar concentration of 100 $\mu$M, were independently incubated with 20 $\mu$g PDE4 enzyme and 1 $\mu$M cAMP containing 0.01 $\mu$M [$^3$H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE5: PDE5 partially purified from human platelets was used. A racemic mixture of flosequinan, and each enantiomer of flosequinan, all at a molar concentration of 100 $\mu$M, were independently incubated with 120 $\mu$g PDE5 enzyme and 1 $\mu$M cGMP containing 0.01 $\mu$M [$^3$H]cGMP in Tris buffer pH 7.5 for 20 minutes at 30° C. The reaction was terminated by boiling for 2 minutes, and the resulting GMP was converted to guanosine by addition of 10 mg/ml snake venom nucleotidase and further incubation at 30° C. for 10 minutes. Unhydrolyzed cGMP was bound to AGI-X2 resin, and the remaining [$^3$H]guanosine in the aqueous phase was quantitated by scintillation counting.

PDE6: PDE6 partially purified from bovine retinal rod and activated by trypsin was used. A racemic mixture of flosequinan, and each enantiomer of flosequinan, all at a molar concentration of 100 $\mu$M, were independently incubated with 0.2 $\mu$g/ml active PDE6 and 100 $\mu$M cGMP containing 0.1 $\mu$M [$^3$H]cGMP in Tris buffer pH 7.5 for 20 minutes at 30° C. Each reaction was terminated by boiling for 2 minutes. The resulting GMP was converted to guanosine by addition of 10 mg/ml snake venom nucleotidase, and further incubated at 30° C. for 10 minutes. Unhydrolyzed cGMP was bound to AGI-X2 resin, and [$^3$H]guanosine remaining in the aqueous phase was quantitated by scintillation counting.

The results of the above PDE assays are presented in the following table. The assay results indicate that the (+) enantiomer of flosequinan demonstrated more PDE1 and PDE3 inhibitory activity when compared with the (−) enantiomer of flosequinan. These empirical results could not be predicted.

| Target Phosphodiesterase | % Inhibition w/ 100 $\mu$M racemic mixture of flosequinan | % Inhibition w/ 100 $\mu$M (+)- flosequinan | % Inhibition w/ 100 $\mu$M (−)- flosequinan |
|---|---|---|---|
| PDE1 | 31 | 28 | 11 |
| PDE2 | 18 | 18 | 13 |
| PDE3 | 26 | 32 | 5 |
| PDE4 | 24 | 6 | 1 |
| PDE5 | 11 | 17 | 10 |
| PDE6 | 21 | 22 | 21 |

EXAMPLE 4

This example describes how compounds of general formula (I) can be prepared.

a. 7-fluoro-1-methyl-4-oxo-1,4-dihydroquinolone-3-carboxamide can be prepared as described in Example 1 of U.S. Pat. No. 4,855,291.

(i) A mixture of ethyl 7-fluoro-4-hydroxyquinoline-3-carboxylate (4.7 g), anhydrous potassium carbonate (3.0 g), dimethyl sulphate (2.52 g) and butanone (200 ml) can be boiled under reflux for 14 hours. The solvent can be evaporated and the residue can be triturated with dichloromethane (150 ml). The mixture can be filtered and the filtrate evaporated to a-small volume. Diethyl ether can be added, causing a solid to precipitate. The solid can be collected, washed with ether, dried and recrystallized from industrial methylated spirit to give the compound ethyl 7-fluoro-1-methyl-4-oxo-1,4-dihydroquinoline-3-carboxylate, m.p. 164–166° C.

(ii) A mixture of 19.0 g of the above carboxylate ester, aqueous ammonia (specific gravity 0.88, 750 ml) and capryl alcohol (2 drops) can be stirred on a steam bath for 1.5 hours, then cooled to room temperature. The solid product can be collected by filtration and recrystallized from industrial methylated spirit/water 3:2 to give the compound 7-fluoro-1-methyl-4-oxo-1,4-dihydroquinoline-3-carboxamide, m.p. 317–318° C.

b. 4-methyl-7-oxo-4,7-dihydrothieno[3,2-b]pyridine-6-carboxamide can be prepared as described in Example 1 of U.S. Pat. No. 4,877,793.

(i) Dimethyl sulphate (3.9 ml) can be added to a stirred solution of ethyl 7-hydroxythieno[3,2-b]-pyridine-6-carboxylate (4.63 g) and potassium hydroxide (3.5 g) in water (50 ml) at 0–5° C. More water (20 ml) can be added and the mixture can be stirred at ambient temperature for 24 hours. The solid product can be collected by filtration, washed with water and dried to give the compound ethyl 4-methyl-7-oxo-4,7-dihydrothieno[3,2-b]pyridine-6-carboxylate, m.p. 122–128° C.

(ii) A mixture of 3.0 g of the product from (i) above and aqueous ammonia (specific gravity 0.880, 60 ml) can be stirred and heated on a steam bath. Effervescence will occur and octan-1-ol (2 ml) and more aqueous ammonia (specific gravity 0.880, 20 ml) can be added and heating on the steam bath can be continued overnight. The mixture can then be cooled to ambient temperature and the solid product collected by filtration, dried and crystallized from industrial methylated spirit to give the compound 4-methyl-7-oxo-4,7-dihydrothieno[3,2-b]pyridine-6-carboxamide, m.p. 255–258° C.

c. 4-methyl-6-methylsulphinyl-7(4H)-thieno[3,2-b]pyridinone can be prepared as described in Example 2 of U.S. Pat. No. 4,710,506.

A solution of 3-chloroperbenzoic acid (85%; 1.63 g) in dichloromethane (60 ml) can be added dropwise during 20 minutes to a stirred solution of 4-methyl-6-methylthio-thieno[3,2-b]pyrid-7(4H)-one (2.0 g) in dichloromethane (60 ml) at 0–5° C. After 4 hours, more 3-chloroperbenzoic acid (0.15 g) in dichloromethane (10 ml) can be added and the mixture stirred overnight at ambient temperature. More 3-chloroperbenzoic acid (0.15 g) in dichloromethane (10 ml) can be added and the mixture can again be stirred overnight at ambient temperature. The resulting solution can be extracted with saturated aqueous sodium bicarbonate solution (5×150 ml) and saturated aqueous sodium chloride solution (1×150 ml) and the organic phase can be discarded. The aqueous extracts are combined and extracted with dichloromethane (5×100 ml). The organic extracts are combined, dried over anhydrous magnesium sulphate and evaporated to give a solid product. This product can be crystallized from industrial methylated spirit to give the compound: 4-methyl-6-methylsulphinyl-thieno[3,2-b]pyrid-7(4H)-one, m.p. 174–176° C.

d. 7-chloro-1-methyl-3-methylsulphamoyl-4-quinolone can be prepared as described in Example 4 of U.S. Pat. No. 4,772,614.

(i) 7-Chloro-1-methyl-4-quinolone (6.9 g) and chlorosulphonic acid (14 ml) can be stirred and heated at 140° C. for 2 hours. The reaction mixture can be cooled to room temperature and carefully added dropwise to ice water (200 ml). The solid which forms can be collected, washed with water and dried in air to give the compound 7-chloro-1-methyl-4-oxo-1,4-dihydroquinoline-3-sulphonyl chloride, m.p. >300° C.

(ii) 6.5 g of the above sulphonyl chloride and aqueous methylamine (30% w/v; 220 ml) can be stirred at room temperature for 3 hours. The resulting solid can be collected, washed with water and crystallized from dichloromethane/industrial methylated spirit 1:1. The product can be collected and partitioned between water (200 ml) and dichloromethane (200 ml). The organic layer can be separated, dried over anhydrous sodium sulphate and evaporated to dryness. The residue can be crystallized from industrial methylated spirit to give the compound 7-chloro-1,N-dimethyl-4-oxo-1,4-dihydroquinoline-3-sulphonamide, m.p. 220–223° C.

e. 7-chloro-1-methyl-4-oxo-1,4-dihydroquinoline-3-carboxamide can be prepared as described in Example 4 of U.S. Pat. No. 4,855,291.

A mixture of ethyl 7-chloro-1-methyl-4-oxo-1,4-dihydroquinoline-3-carboxylate (5.0 g) and aqueous ammonia (specific gravity 0.88, 100 ml) can be stirred and heated on a steam bath for 3.5 hours. More aqueous ammonia (100 ml) can be added and heating continued for a further 21 hours. The mixture can be cooled in ice. The solid product can be collected by filtration and dried to give the compound 7-chloro-1-methyl-4-oxo-1,4-dihydroquinoline-3-carboxamide, m.p. >240° C.

We claim:

1. A method of treating the symptoms of Tourette Syndrome in a subject with symptoms of Tourette Syndrome, wherein said subject is free of cardiac disease and is not being treated with a drug that causes hypotensive effects; comprising administering an effective amount of flosequinan to said subject whereby said symptoms are reduced.

2. The method of claim 1, wherein said flosequinan is present as a racemic mixture.

3. The method of claim 1, wherein said flosequinan is a purified enantiomer.

4. The method of claim 1, wherein said flosequinan is introduced into said subject by oral administration.

5. The method of claim 4, wherein said subject is an adult human and said oral administration comprises up to approximately 200 milligrams of flosequinan.

6. The method of claim 1, wherein said flosequinan is introduced into said subject cutaneously.

7. The method of claim 1, wherein said flosequinan is introduced into said subject intravenously.

8. The method of claim 1, wherein said subject is male.

9. The method of claim 1, wherein said subject is female.

10. The method of claim 1, wherein said subject is an adult.

11. The method of claim 1, wherein said subject is a child.

12. A method of treating the symptoms of Tourette Syndrome in a subject with symptoms of Tourette Syndrome, wherein said subject is free of cardiac disease and is not being treated with a drug that causes hypotensive effects, comprising administering an effective amount of cilostazol to said subject whereby said symptoms are reduced.

13. The method of claim 12, wherein said cilostazol is introduced into said subject by oral administration.

14. The method of claim 13, wherein said subject is an adult human and said oral administration comprises up to approximately 100 milligrams of cilostazol twice a day.

15. The method of claim 12, wherein said cilostazol is introduced into said subject cutaneously.

16. The method of claim 12, wherein said subject is male.

17. The method of claim 12, wherein said subject is female.

18. The method of claim 12, wherein said subject is an adult.

19. The method of claim 12, wherein said subject is a child.

* * * * *